United States Patent [19]

Goforth

[11] Patent Number: 4,647,918
[45] Date of Patent: Mar. 3, 1987

[54] MULTI-EVENT NOTIFICATION SYSTEM FOR MONITORING CRITICAL PRESSURE POINTS ON PERSONS WITH DIMINISHED SENSATION OF THE FEET

[76] Inventor: William P. Goforth, 11903 Las Vegas, San Antonio, Tex. 78233

[21] Appl. No.: 693,001

[22] Filed: Jan. 16, 1985

[51] Int. Cl.$^4$ ............................................. G08B 23/00
[52] U.S. Cl. ..................................... 340/573; 128/779; 73/172
[58] Field of Search ................ 340/573, 666; 128/774, 128/779; 364/413, 558; 73/172

[56] References Cited

U.S. PATENT DOCUMENTS

| | | | |
|---|---|---|---|
| 2,290,387 | 7/1942 | Schwartz | 128/779 X |
| 4,073,292 | 2/1978 | Edelman . | |
| 4,092,633 | 5/1978 | Fletcher et al. | 340/573 X |
| 4,136,682 | 1/1979 | Pedotti | 128/779 |
| 4,178,916 | 12/1979 | McNamara . | |
| 4,179,692 | 12/1979 | Vance | 340/573 |
| 4,195,643 | 4/1980 | Pratt, Jr. | 128/779 |
| 4,365,637 | 12/1982 | Johnson . | |
| 4,426,884 | 1/1984 | Polchaninoff . | |
| 4,554,930 | 11/1985 | Kress | 73/172 X |

OTHER PUBLICATIONS

"An Automated Accelerometry System for Gait Analysis", Journal of Biomerics, 1977, vol. 10, pp. 367-375.

Primary Examiner—James L. Rowland
Assistant Examiner—Brian R. Tumm
Attorney, Agent, or Firm—Sisson & Smith

[57] ABSTRACT

A multi-event notification system for monitoring preselected critical pressure points, as a function of pressure in a lapsed time, on the feet of persons being diagnosed as having diminished sensation in the feet. A plurality of pressure transducers for measuring and monitoring pressure at any number of points on a patient's foot are electrically connected to a microprocessor. The processor is programmable to integrate when pressure is sensed at the sensing points over a preselected time interval. If any of a number of the sensing points reaches a preselected threshold of pressure events over the given time interval, an alarm indicator connected to the processor provides an alarm indication that the total number of pressure events exceeds the threshold limit.

4 Claims, 4 Drawing Figures

U.S. Patent   Mar. 3, 1987   Sheet 1 of 2   4,647,918

MULTI-EVENT NOTIFICATION SYSTEM FOR MONITORING CRITICAL PRESSURE POINTS ON PERSONS WITH DIMINISHED SENSATION OF THE FEET

BACKGROUND OF THE INVENTION

This invention relates to a multi-event notification system for monitoring pre-selected critical pressure points, as a function of pressure in a lapsed time, on the feet of persons who have been diagnosed as having diminished sensation in the feet, especially diabetes mellitus.

There have been a number of inventions which have been specifically aimed at problems related to diabetes. However, most of these inventions have related to devices for monitoring conditions indicating the onset or existence of insulin shock. Physiological conditions associated with insulin shock include lowered skin resistance, a drop in body temperature, a reduced ability to respond to light changes (eye pupil dilation lag), and, in heavy shock, increased heart beat, labored breathing, and convulsions. If allowed to develop, such shock can lead to a heart attack and death. The prior art devices have primarily been aimed at detecting any number of these various physiological conditions. Specifically, U.S. Pat. No. 4,365,639 discloses a perspiration indicating alarm for diabetics. In this device any increase in perspiration is detected and signals an alarm. U.S. Pat. No. 4,178,916 to a diabetic insulin alarm system discloses a system that is worn by a diabetic person which responds to the wearer's abnormal skin resistance or temperature and signals this indication to the wearer. U.S. Pat. No. 4,073,292 to a control apparatus for the automatic treatment of diabetes discloses an invention for monitoring the body's sugar level during a given period and injecting suitable doses of insulin to suppress any excess amount of glucose.

The present invention is directed at another significant problem encountered by people suffering from diabetes. Those persons who have diabetes in such severity as to have poor sensation in the lower extremities with either partial or total loss of feeling currently have no means, other than visible observation, of determining whether a skin ulceration is occurring in skin of the foot. This problem is further compounded because ulcers or open wounds are very slow to heal in the diabetic where metabolism and blood circulation is poor. Once an ulcer or open wound has been discovered, the diabetic is required to stay off the foot or feet, that is, remove the pressure from where the wound is located. In some situations this requires days, weeks, or even months. The duration of time which the patient must remain off of his feet is dependent upon the rate of healing of the ulcer which in turn is dependent upon the blood flow to the damaged area.

Such ulcers or open wounds are almost invariably the result of pressure applied to a particular point on the front through standing or walking over a period of time. Since a diabetic has only partial or no feeling in the feet, the point at which such damage occurs is not known to the diabetic at the time of occurrence. There is no reliable notification system in existence today that can alert the diabetic that such damage is about to occur. If the damage is to be prevented, the diabetic must remove the pressure from the area where the ulcer or wound is about to occur.

While there have been sensors developed which measure the forces exerted by the human body during such movements as walking, jogging, and orthopedic testing, none have been directed toward the particular problems encountered by the diabetic who may experience low levels of pressure over extended time periods. U.S. Pat. No. 4,426,884 discloses an invention which relates to a sensor for sensing foot pressures and is incorporated herein by reference.

The instant invention is a reliable, accurate, mobile, self-contained, automatic, multi-event twenty-four hour per day alert system for the diabetic. The system is inconspicuously attachable to the person of the diabetic for notifying the diabetic that the pressure/time threshold is about to be reached and that if pressure is not removed an ulcer or wound could occur. The present invention serves a significant preventative function and prevents much human suffering.

SUMMARY OF THE INVENTION

The invention is a system for sensing pressure and time and comprises a pressure sensitive sensor or pressure transducers for measuring and monitoring pressure at any number of points on the patient's foot or feet. A microprocessor is programmed to integrate discrete pounds per square inch pressure over preselected time intervals for a given number of the sensors located on a foot pad. The device also "subtracts" for time periods during which no pressure is detected. A notification device produces a visible and audible indication which can be heard and/or seen by the user when any of a number of the sensing points reaches a preselected threshold of pressure over a time interval as computed by the microprocessor. The device has a self-test feature which allows the patient to verify that the unit is functional. The device is powered by batteries contained in the processor and/or sensor units.

DETAILED DESCRIPTION OF THE PREFERRED EMBODIMENT

Figure 1:
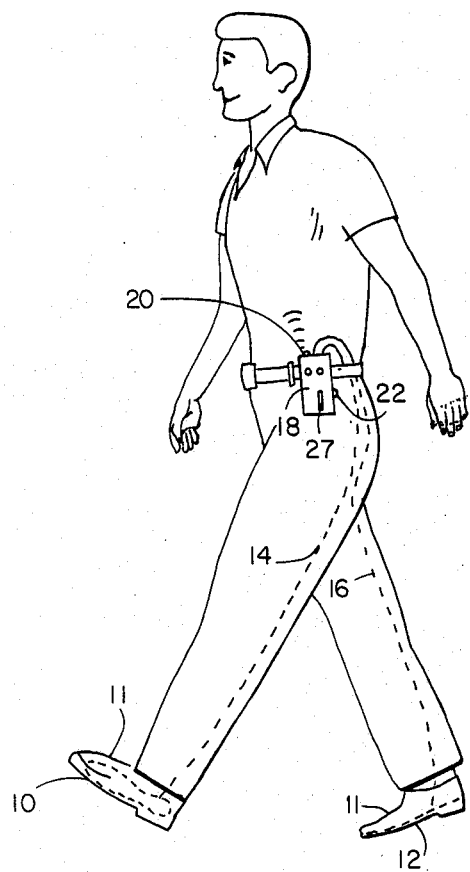
FIG. 1 is a diagrammatic perspective view showing the location of the various elements of the invention.

The present invention contains few essential elements as shown in FIG. 1. Foot sensor pads 10 and 12 each having a multiplicity of sensing elements located thereon are electrically and detachably connected by flat wires 14 and 16 to microprocessor unit 18 via a universal, multi-pin adapter 17. Microprocessor 18 is programable to integrate the electrical signals received from the foot sensor pads 10 and 12 over a given period of time to indicate when a threshold level has been reached. The user is notified when this threshold is reached by either an audible indicator 20 and/or a visible indicator light 22.

Figure 4:
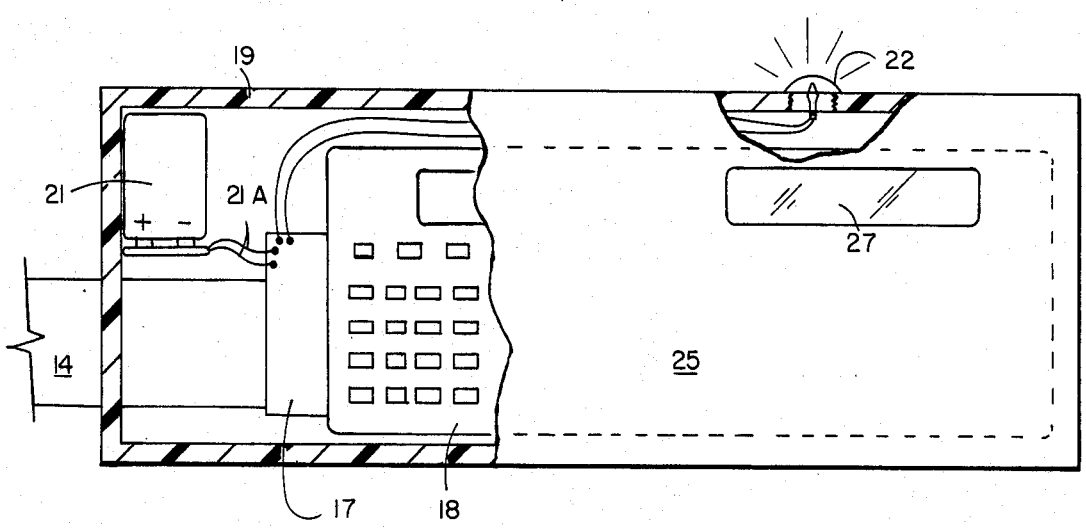
FIG. 4 is a cut-away perspective view of the microprocessor of the invention.

FIG. 4 shows the processor 18 of the invention within housing 19 with its associated universal, multi-pin adapter 17 and battery power supply 21 for supplying power to the pressure transducers 24 in foot sensor pads 10 and 12. Processor 18 has its own integral battery power supply. Housing 19 has a detachable cover 25 with an opening or window 27 formed therein to enable the user to see the processor's digital readout. Battery 21 is electrically wired via leads 21A to the universal, multi-pin adapter 17 such that power is supplied to the pressure transducers via flat wire 14. The processor's internal power supply provides the power to illuminate the bulb of visible indicator 22 and produces its own internal audible beeping sound which can be heard through housing 19 via opening 27.

Figure 2:
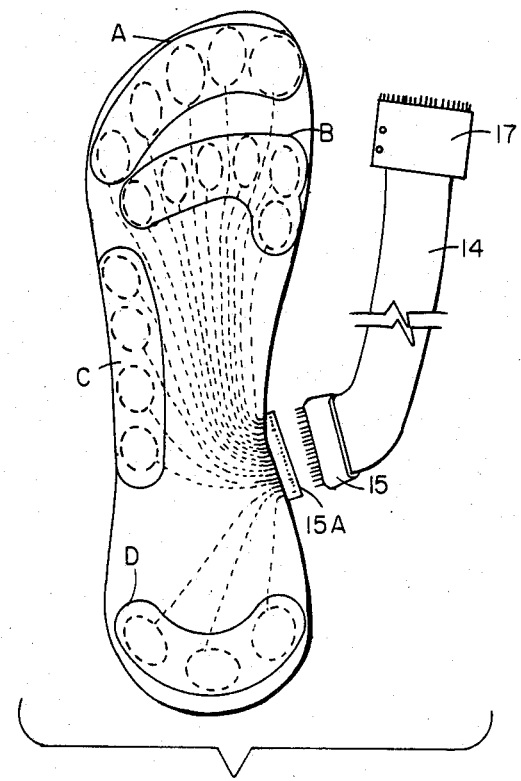
FIG. 2 is a perspective view showing the positioning of the foot sensor pad of the invention.

FIG. 2 shows foot sensor pad 10 inserted within shoe 11 and beneath foot 13. Extending from the side of foot pad 10 and electrically connected thereto via detachable multi-pin adapter 15 is flat wire 14. Flat wire 14 has a multiplicity of separate, fine electrical wires therein and extends up to and is electrically connected to microprocessor 18. The use and structure of such flat wires is commonly known in the art. Similarly, foot sensor pad 12 is depositioned beneath the user's other foot within the other shoe and is electrically connected by means of flat wire lead 16 to microprocessor 18. Alternatively, each foot sensor pad could be electrically connected to a separate processor.

Figure 3:
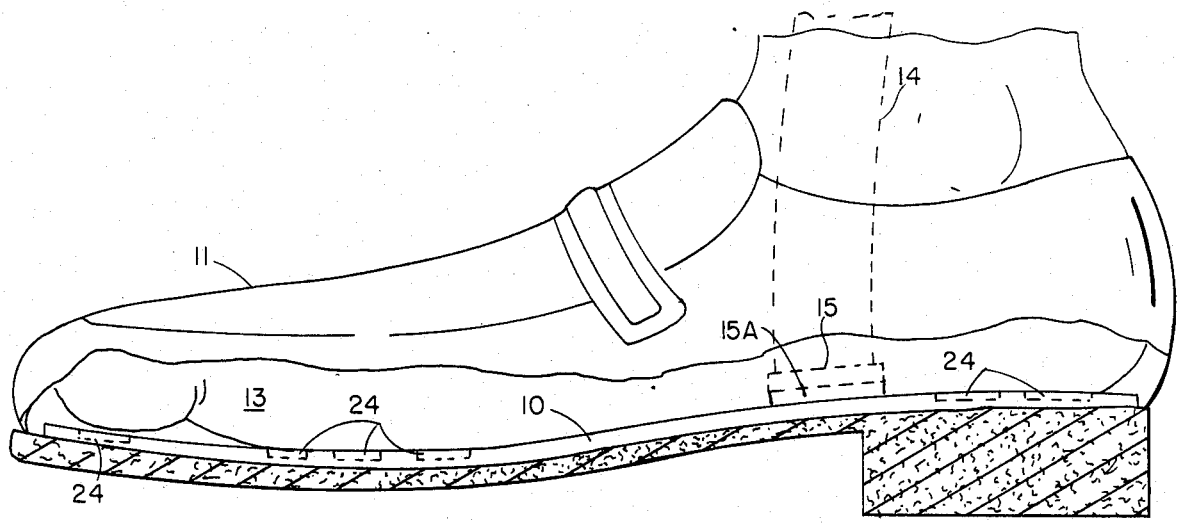
FIG. 3 is a top perspective view of a foot sensor pad of the invention showing a plurality of flexible force sensors grouped thereon.

FIG. 3 is a top view of foot pad 10 showing the location of the numerous flexible force sensors (pressure transducers) 24 as disclosed in U.S. Pat. No. 4,426,884 which are dispositioned throughout foot sensor pad 10 and electrically wired parallel to one another. Specifically, flexible force sensors 24 are grouped into four separate groupings. Grouping A consists of five flexible foot sensors depositioned to be located directly under the toes of the user. Grouping B is a multiplicity of sensors arranged to be dispositioned beneath the forefoot portion of the user's foot. Grouping C extends along the lateral aspect of the user's foot. Grouping D consists of a number of sensors to be dispositioned beneath the heel of the user's foot. All of these flexible force sensors are connected in parallel electrically and each individually provides electrical input to the microprocessing unit 18 via detachable adapter 15 and flat wire 14 when force or pressure or compressive load is applied to the sensor. Each separate transducer (sensor) 24 has a separate electrical connection via flat wire 14 to microprocessor 18. Closure of any one of the switches will cause integration upward by the microprocessor 18. All of the force sensor switches must be open to cause the microprocessor 18 to integrate downward.

The microprocessor 18 provides a doctor with a capability of being able to establish integration rates and threshold limits for each patient's requirements. The microprocessor has an accumulator which registers each closure of each force sensor circuit. In order for the accumulator to register the closure event, the closure must extend for at least one-tenth of a second. This division of time is necessary to accommodate the normal walking gait during which time the weight of the patient may be on his foot for only a fraction of a second. It is envisioned that shorter closure periods of about 0.05 seconds may be appropriate. The doctor may further factor or multiply the value of each closure via the microprocessor to accommodate for those patients having particularly sensitive skin or who are particularly susceptible to ulceration. By factoring the closure increment, the doctor is capable of increasing the significance of each closure event for each particular patient, and further allows the same force sensors to be used with all patients.

When the patient removes pressure from the flexible force sensor, as when he takes his weight off his feet, the electrical circuit is opened. The accumulator in the microprocessor decrements one unit for each full second that all of the flexible force sensors are open. No credit is given for fractions of a second.

If a doctor finds that a particular patient is more susceptible to ulceration of the foot in a particular location, e.g., the lateral aspect of the foot, then the doctor may factor the closure increment more for closures in grouping C than he factors groupings A, B, and D. Likewise, he can program the accumulator to decrement when all sensors in only a particular grouping or groupings are open for one full second.

Additionally, the doctor establishes the threshold limit at which the audible alarm is sounded or the visible indicator light flashes. When the accumulator reaches this threshold value or "T" value, then the alarm is sounded, warning the patient to get his weight off his feet. For each increment unit above this threshold value, the alarm continues to sound. The microprocessor is equipped with a muting function to eliminate the audible sound but the microprocessor continues to provide the visual blinking indicator light.

Once the patient takes his weight off his feet and all of the appropriate flexible force sensor circuits are opened, the accumulator will begin to decrement as indicated above. Once the total increment unit (or sensing events) is below the threshold value "T" and the total of sensing events reaches a predetermined reset value, "R", then the patient can resume walking, thus placing pressure on and closing the force sensors, without setting off the alarm. Until the accumulator drops below this "R" value, the visible alarm will continue to blink and the audible alarm will continue to beep with each step, i.e., each additionally sensed event, unless muted. Once the "R" value has been reached, the indicator light will be extinguished and a long beep of the audible alarm will occur, notifying the patient that he may resume activity.

In order to allow the patient to verify that the unit is functional, a self-test feature has been included in the device. The self-test will check the operation of the microprocessor and the sensors. To actuate the self-test, the user simply places his weight on the foot being monitored, thus closing a flexible force sensor and observes a visible counter indication in the window 27 of the microprocessor unit housing 25. The counter indicates the number of closure increment units (sensed events) in the accumulator. If the unit is functioning properly, when he takes his weight off of the foot being monitored, the counter will decrease in accumulated units because of the decrementing function heretofore discussed.

While the preferred embodiment of the invention utilizes Radio Shack Model TRS 80 Model PC 2 pocket computer and other comparable units, state of the art computer equipment may result in a microprocessor being an integral part of the foot sensor pads 10 and 12. Such a modification is not beyond the scope of the present invention. Thus, while there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

I claim:

1. A multi-event system for sensing pressure and time that a user of said system is putting pressure on his feet comprising:
    a foot pad having pressure transducers located at selected points beneath said user's foot;
    a microprocessor electrically connected in parallel to said transducers, said microprocessor having a means for registering a total number of sensing events, one of said sensing events occurring whenever any of said transducers senses pressure for longer than a first preselected time interval, said means for registering capable of deducting one of said sensing events from said total number of sensing events whenever a preselected number of said transducers do not sense pressure for longer than a second preselected time interval, said microprocessor having a means for comparing said total number of said sensing events to a threshold limit number of sensing events; and
    an alarm indicator connected to said microprocessor providing an alarm indication whenever said total number of said sensing events exceeds said threshold limit.

2. The invention of claim 1 wherein said microprocessor further has a means for comparing said total number of sensing events to a reset number of sensing events and said alarm indicator providing a second indication whenever said total number of sensing events is less than said reset number of sensing events.

3. The invention of claim 1 wherein said first preselected time interval is each tenth of a second.

4. The invention of claim 3 wherein said second preselected time is each one second.

* * * * *